(12) United States Patent
Hennessy

(10) Patent No.: US 8,197,742 B2
(45) Date of Patent: Jun. 12, 2012

(54) LASER ABLATION PROCESS FOR REMOVING A PORTION OF DILATION ELEMENT FROM A BALLOON

(75) Inventor: Eric R. Hennessy, Lewisville, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 213 days.

(21) Appl. No.: 12/782,439

(22) Filed: May 18, 2010

(65) Prior Publication Data

US 2011/0285059 A1 Nov. 24, 2011

(51) Int. Cl.
*B29C 33/42* (2006.01)

(52) U.S. Cl. ........ 264/400; 264/230; 264/539; 264/482; 264/161; 264/162; 264/163; 264/536; 425/527

(58) Field of Classification Search .................. 264/230, 264/400, 539, 482, 161, 162, 163, 536; 425/527
See application file for complete search history.

(56) References Cited

U.S. PATENT DOCUMENTS

| | | | |
|---|---|---|---|
| 5,599,306 A * | 2/1997 | Klein et al. ............. | 604/103.01 |
| 5,733,301 A | 3/1998 | Forman | |
| 6,719,774 B1 | 4/2004 | Wang | |
| 7,306,616 B2 | 12/2007 | Eidenschink et al. | |
| 2002/0072707 A1* | 6/2002 | Gonzalez et al. ........ | 604/103.06 |
| 2005/0137615 A1 | 6/2005 | Mapes et al. | |
| 2006/0129179 A1* | 6/2006 | Weber et al. ................. | 606/194 |
| 2007/0016278 A1 | 1/2007 | Shippy, III et al. | |
| 2008/0132836 A1* | 6/2008 | Burton et al. ............ | 604/103.08 |

FOREIGN PATENT DOCUMENTS

| | | |
|---|---|---|
| EP | 0 783 897 A2 | 12/1996 |
| WO | WO 03/035158 A2 | 5/2003 |
| WO | WO 2009/114425 A1 | 9/2009 |

OTHER PUBLICATIONS

Search Report for related International Application No. PCT/US2011/036618 mailing date of Aug. 19, 2011.

* cited by examiner

*Primary Examiner* — Christina Johnson
*Assistant Examiner* — Saeed Huda
(74) *Attorney, Agent, or Firm* — Brinks Hofer Gilson & Lione

(57) ABSTRACT

A method is provided for a ablating dilation beads on a balloon with a laser. The laser removes integral dilation beads from the neck regions and/or the tapered regions of a blow molded balloon. Part of the neck portions of the dilation beads may remain on the body of the balloon after the dilation beads have been removed.

20 Claims, 4 Drawing Sheets

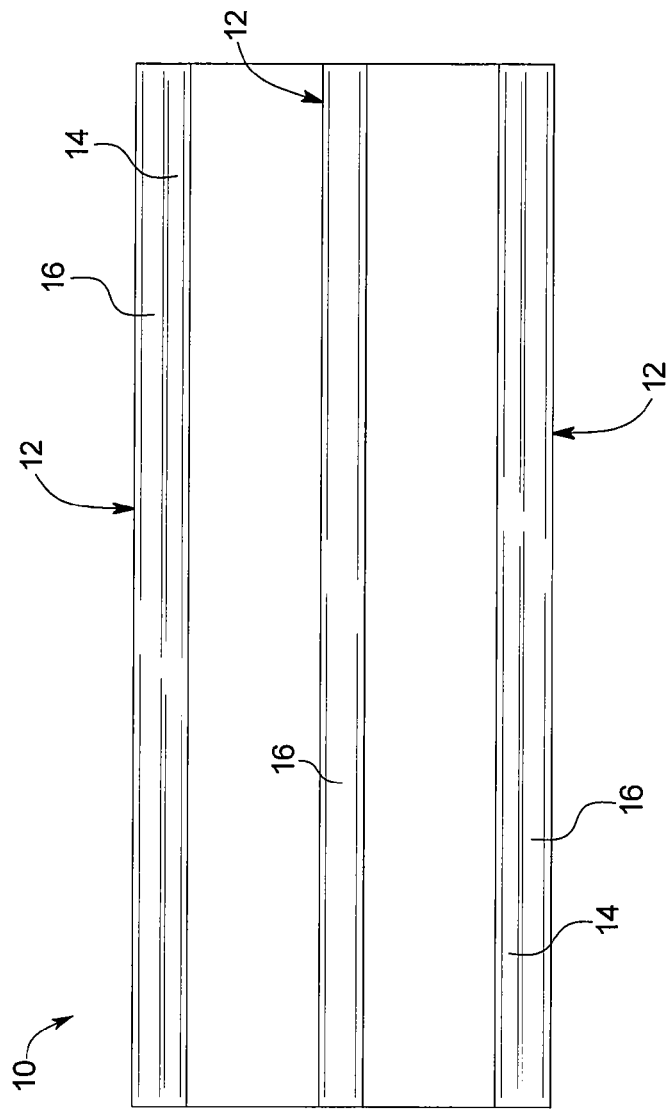
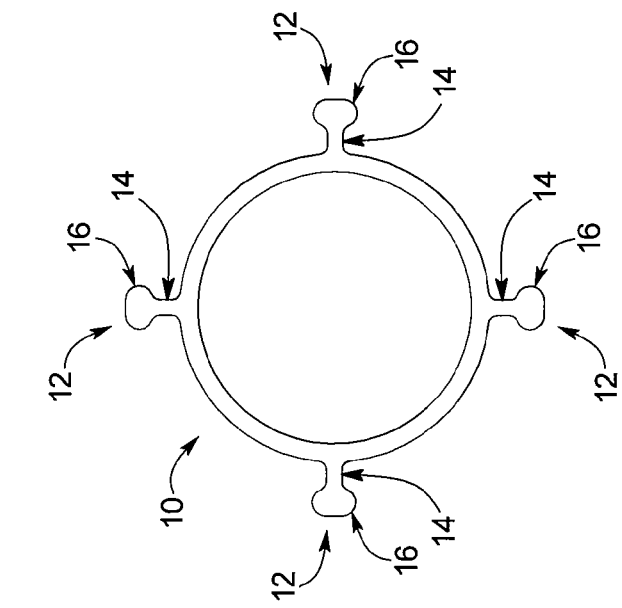

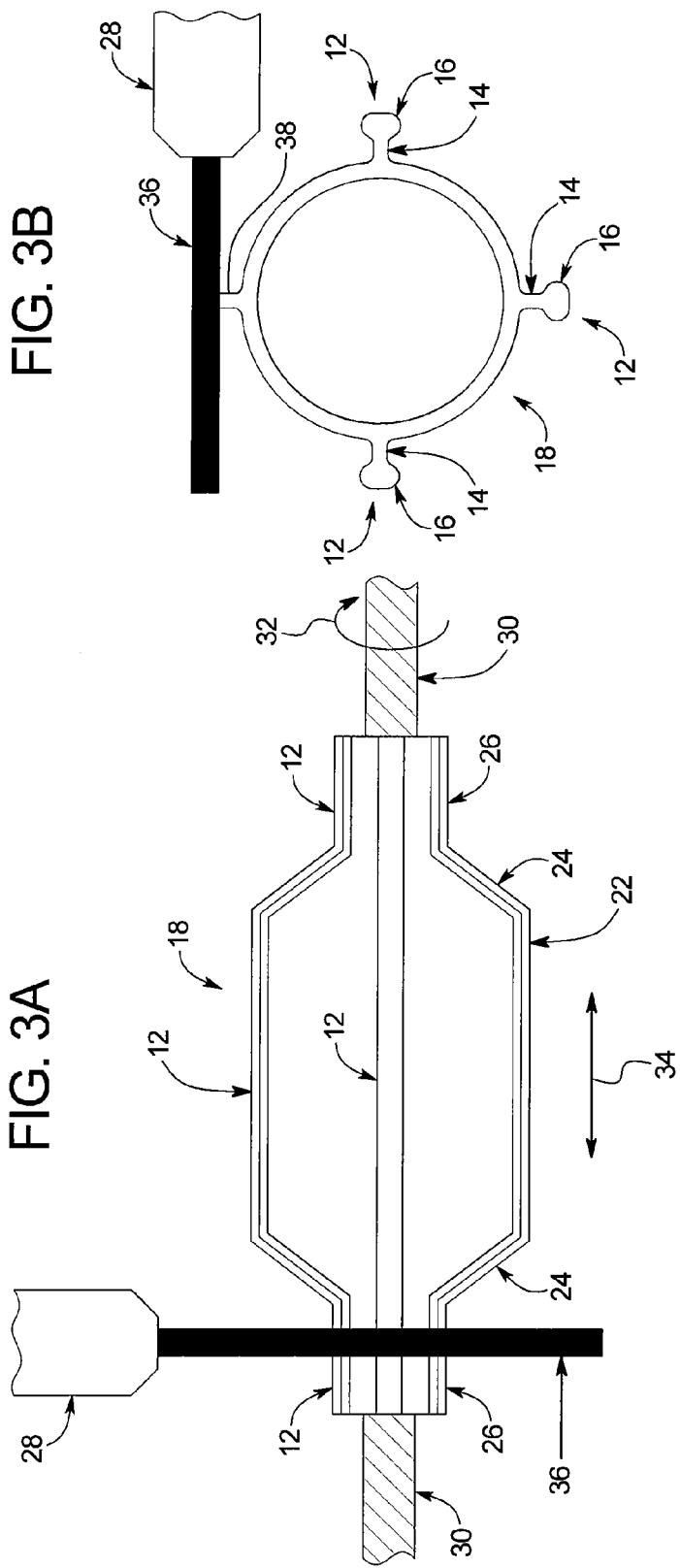
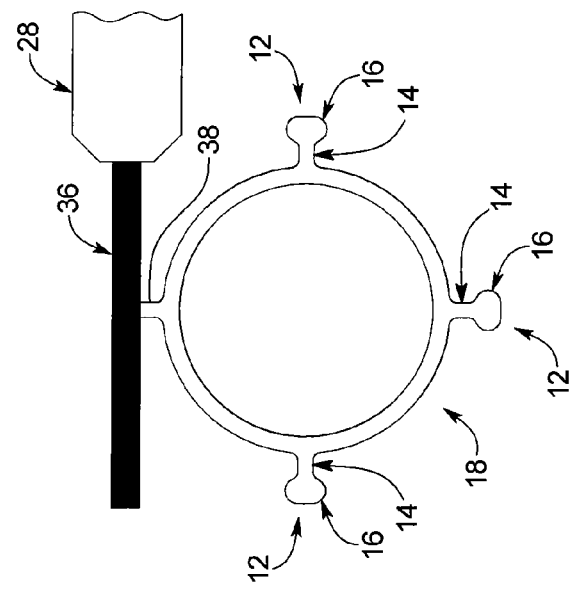

LASER ABLATION PROCESS FOR REMOVING A PORTION OF DILATION ELEMENT FROM A BALLOON

BACKGROUND

The present invention relates generally to medical devices and particularly to a laser ablation process for removing a portion of a dilation element from a balloon.

Balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow).

Although balloon catheters are used in many other procedures as well, vascular angioplasty using a balloon catheter has drawn particular attention from the medical community because of the growing number of people suffering from vascular problems associated with arterial stenosis. This has lead to an increased demand for medical procedures to treat such problems. The widespread frequency of vascular problems may be due to a number of societal changes, including the tendency of people to exercise less while eating greater quantities of unhealthy foods, in conjunction with the fact that people generally now have longer life spans than previous generations. Angioplasty procedures have become a popular alternative for treating arterial stenosis because angioplasty procedures are considerably less invasive than other alternatives. As an example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for vascular treatments, the medical community has turned to angioplasty procedures, in combination with stenting and other procedures, to avoid the problems associated with traditional open surgery. Typically, angioplasty procedures are performed using a balloon-tipped catheter that may or may not have a stent mounted on the balloon (also referred to as a stented catheter). The physician performs the angioplasty procedure by introducing the balloon catheter into a peripheral artery (commonly one of the leg arteries) and threading the catheter to the narrowed part of the artery to be treated. During this stage, the balloon is uninflated and collapsed onto the shaft of the catheter in order to present a low profile which may be passed through the vasculature. Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the body. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure. Although the treatment of stenosed arteries is one common example where balloon catheters have been used, this is only one example of how balloon catheters may be used and many other uses are also possible.

One problem that may be encountered with conventional angioplasty techniques is the proper dilation of stenosed regions that are hardened and/or have become calcified. Stenosed regions may become hardened for a variety of reasons, such as the buildup of atherosclerotic plaque or other substances. Hardened regions of stenosis can be difficult to completely dilate using conventional balloons because hardened regions tend to resist the expansion pressures applied by conventional balloon catheters.

One solution that has been offered for dilating hardened stenoses is special balloon catheters with dilation wires or beads that extend along the length of the balloon. The dilation wires and/or beads focus that dilation pressure of the balloon onto the narrower contact area between the dilation wire or bead and the vessel wall. As a result, the increased, focused pressure may crack and/or break up the hardened stenosis, thereby allowing the vessel lumen to be expanded.

However, it is more difficult to manufacture balloon catheters with integral dilation beads. One problem that has been encountered in the manufacture of these types of balloon catheters is the dilation beads make it more difficult to bond the balloon to the catheter. The dilation beads can also interfere with the delivery system during use of the balloon catheter in a dilation procedure and can prevent the balloon from smoothly folding into the deflated configuration.

Accordingly, the inventor believes it would be desirable to provide a manufacturing process to remove parts of an integral bead from a balloon catheter.

SUMMARY

A processes is described for removing an integral dilation bead from a balloon with a laser. The balloon is mounted on a mandrel, and the mandrel and laser are rotated and translated relative to each other. The laser ablates the head portion of the dilation bead and part of the neck portion of the dilation bead. Thus, part of the neck portion may remain on the balloon after the dilation bead has been removed.

The invention may include any of the following aspects in various combinations and may also include any other aspect described below in the written description or in the attached drawings.

A method of manufacturing a balloon catheter, comprising:
extruding a parison comprising a bead along an entire length of an outer surface of the parison, the bead comprising a head portion and a neck portion connecting the head region to the outer surface;
blow molding the parison to form an expanded balloon configuration comprising a working diameter region, a tapered region at each end of the working diameter region, and a neck region at each end of the tapered regions, the working diameter region being larger in diameter than the neck regions and the tapered regions providing transitions between the working diameter region and the neck regions;
wherein the neck portion of the bead comprises a width less than a width of the head portion of the bead after blow molding;
mounting the blow molded balloon on a mandrel extending through an inner lumen of the neck regions;
positioning the mandrel and the blow molded balloon relative to a laser beam so that the laser beam is oriented 90° from the mandrel and is offset from the mandrel so that a width of the laser beam covers the entirety of the head portion and only part of the neck portion;

translating the laser beam and the mandrel relative to each other while the laser beam is activated, the laser beam thereby passing along each of the neck regions and ablating the entirety of the head portion and only part of the neck portion along the neck regions, a part of the neck portion remaining on the neck regions after ablating the beam;

removing the mandrel from the blow molded balloon after ablating the bead; and inserting a catheter through the inner lumen of the neck regions and bonding the neck regions to the catheter.

The method further comprising rotating the laser beam and the mandrel relative to each other at the same time the laser beam and the mandrel are translated relative to each other, wherein more than one of the bead disposed around a circumference of the neck regions are partially ablated during each full rotation.

The method further comprising rotating the laser beam and the mandrel relative to each other a full rotation and translating the laser beam and the mandrel relative to each other a distance less than the width of the laser beam for the full rotation, wherein more than one of the bead disposed around a circumference of the neck regions are partially ablated during the full rotation.

The method further comprising translating the laser beam and the mandrel relative to each other at the same time the offset between the laser beam and the mandrel is changed, the laser beam thereby passing along at least part of the tapered regions and ablating the entirety of the head portion and only part of the neck portion along the tapered regions, a part of the neck portion remaining on the tapered regions after ablating the beam.

The method further comprising disposing heat shrink tubing over the neck regions after the catheter is inserted through the inner lumen of the neck regions and heating the heat shrink tubing and the neck regions, the part of the neck portion remaining on the neck regions after ablating the beam thereby being substantially reformed into the neck regions.

The method wherein the parison is extruded from a nylon material.

The method wherein the width of the neck portion is about 0.010" to about 0.020" and the width of the head portion is about 0.015" to about 0.030".

The method wherein a height of the neck portion is about 0.010" to about 0.025" and a height of the head portion is about 0.010" to about 0.020".

The method wherein the width of the laser beam is about 0.020" to about 0.045".

The method wherein a wavelength of the laser beam is about 10 µm to about 12 µm.

The method wherein a focal length of the laser beam is about 3 mm to about 10 mm.

The method wherein a power of the laser beam is about 1 W to about 2 W.

The method wherein a rate of travel of the laser beam is about 0.1 mm/s to about 1 mm/s.

The method further comprising rotating the laser beam and the mandrel relative to each other a full rotation and translating the laser beam and the mandrel relative to each other a distance less than the width of the laser beam for the full rotation, wherein more than one of the bead disposed around a circumference of the neck regions are partially ablated during the full rotation, and disposing heat shrink tubing over the neck regions after the catheter is inserted through the inner lumen of the neck regions and heating the heat shrink tubing and the neck regions, the part of the neck portion remaining on the neck regions after ablating the beam thereby being substantially reformed into the neck regions.

The method further comprising translating the laser beam and the mandrel relative to each other at the same time the offset between the laser beam and the mandrel is changed, the laser beam thereby passing along at least part of the tapered regions and ablating the entirety of the head portion and only part of the neck portion along the tapered regions, a part of the neck portion remaining on the tapered regions after ablating the beam.

The method wherein the parison is extruded from a nylon material, the width of the neck portion being about 0.010" to about 0.020", the width of the head portion being about 0.015" to about 0.030", a height of the neck portion being about 0.010" to about 0.025", a height of the head portion being about 0.010" to about 0.020", and the width of the laser beam being about 0.020" to about 0.045".

The method wherein a wavelength of the laser beam is about 10 µm to about 12 µm, a focal length of the laser beam is about 3 mm to about 10 mm, a power of the laser beam is about 1 W to about 2 W, and a rate of travel of the laser beam is about 0.1 mm/s to about 1 mm/s.

The method wherein the parison is extruded from a nylon material, the width of the neck portion being about 0.010" to about 0.020", the width of the head portion being about 0.015" to about 0.030", a height of the neck portion being about 0.010" to about 0.025", and a height of the head portion being about 0.010" to about 0.020".

The method wherein the width of the laser beam is about 0.020" to about 0.045", a wavelength of the laser beam is about 10 µm to about 12 µm, a focal length of the laser beam is about 3 mm to about 10 mm, and a power of the laser beam is about 1 W to about 2 W.

The method further comprising disposing heat shrink tubing over the neck regions after the catheter is inserted through the inner lumen of the neck regions and heating the heat shrink tubing and the neck regions, the part of the neck portion remaining on the neck regions after ablating the beam thereby being substantially reformed into the neck regions.

BRIEF DESCRIPTION OF SEVERAL VIEWS OF THE DRAWINGS

The invention may be more fully understood by reading the following description in conjunction with the drawings, in which:

FIG. 1A is an end view of an extruded parison;

FIG. 1B is a side view of the extruded parison;

FIG. 3A is a side view of the blow molded balloon mounted on a mandrel and positioned relative to a laser;

FIG. 3B is an end view of the blow molded balloon, showing the offset position of the laser.

DETAILED DESCRIPTION

Figure 2:
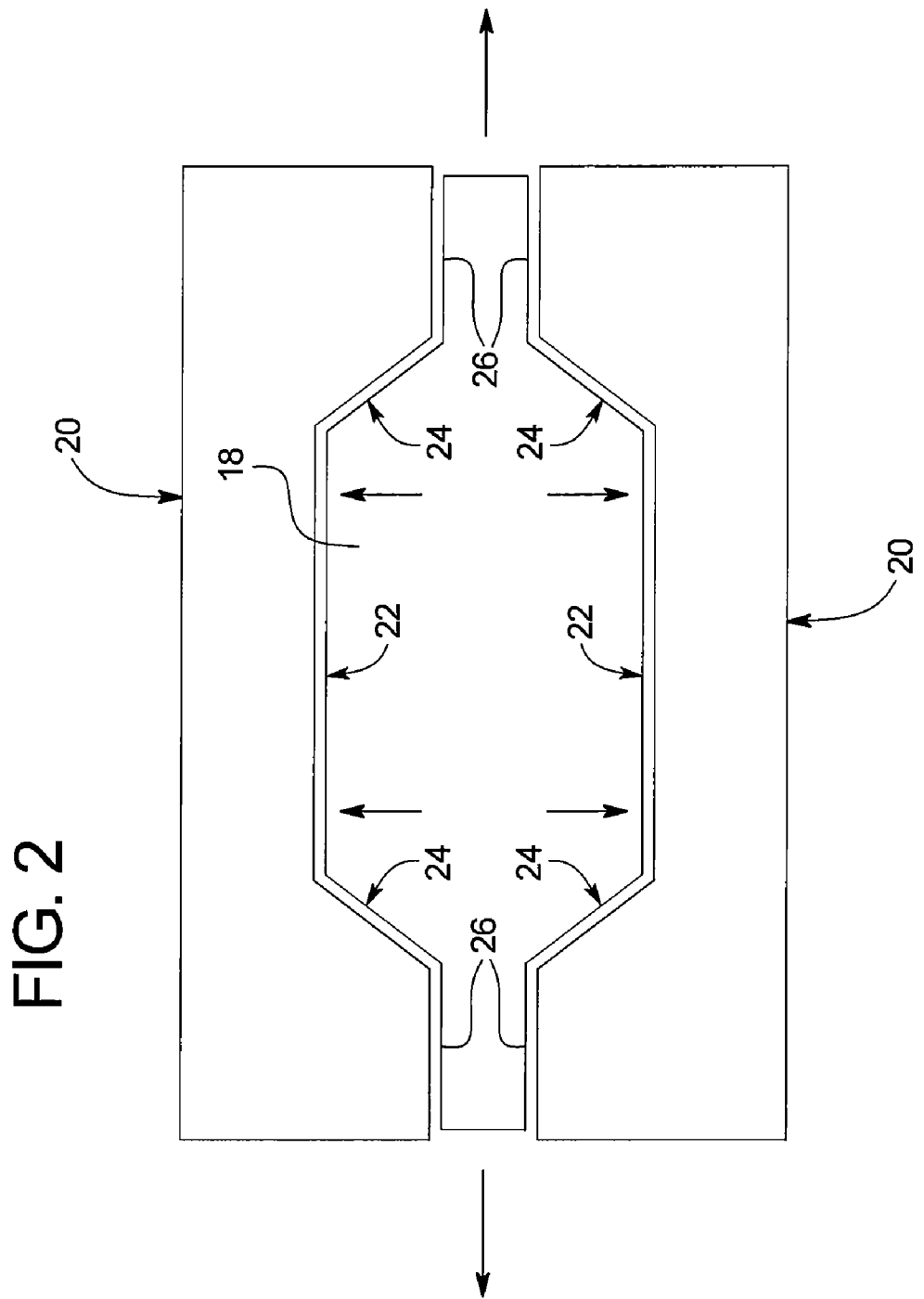
FIG. 2 is a side view of a blow molded balloon in a mold.
Figure 4:
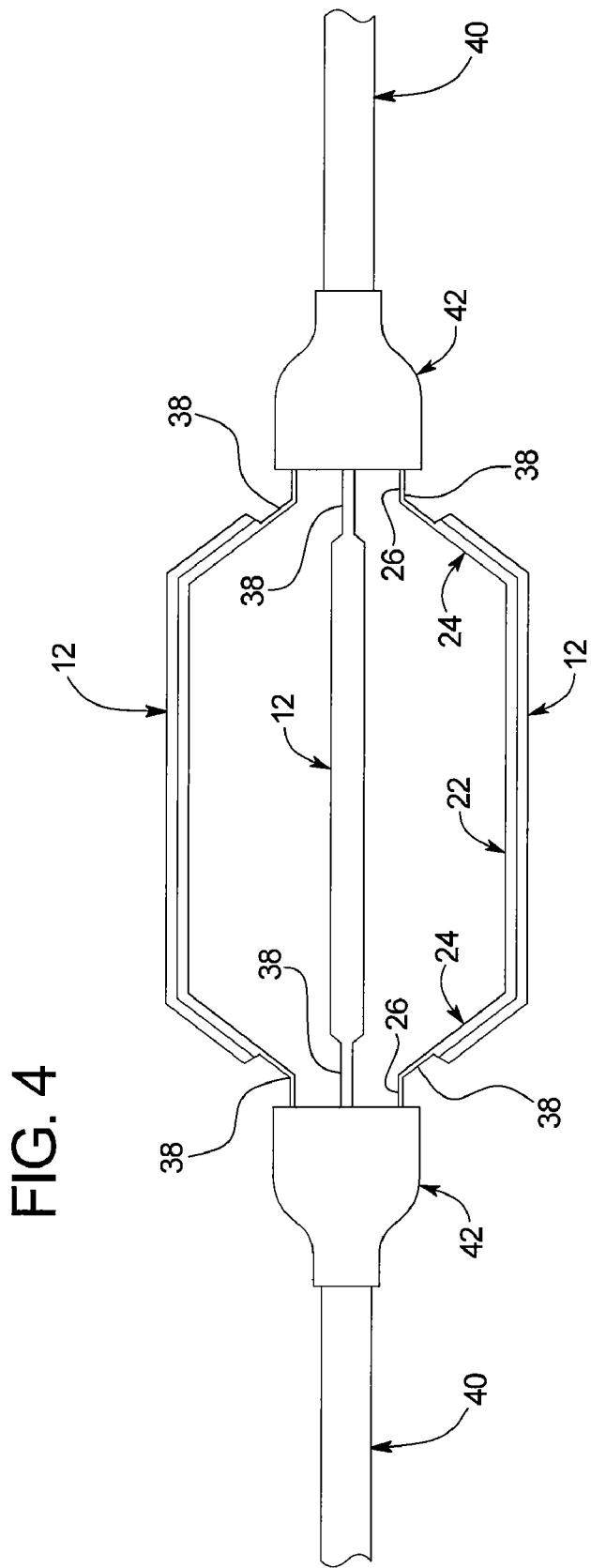
FIG. 4 is a side view of the blow molded balloon affixed to a catheter.

Referring now to the figures, and particularly to FIGS. 1A-1B, a parison 10 for a balloon with integral dilation beads 12 is shown. Preferably, the parison 10 is made from a nylon material. The parison 10 may be formed by extruding a continuous tube of nylon material with integral beads 12 extending along the entire length of the parison 10. Although the size and shape of the dilation beads 12 may be altered slightly by subsequent manufacturing steps, such as blow molding as described below, it is desirable for the width of the neck portion 14 of the bead 12 to be about 0.010" to about 0.020" and the height of the neck portion 14 to be about 0.010" to about 0.025" on the finished balloon catheter. It is also desirable for the width of the head portion 16 of the bead 12 to be about 0.015" to about 0.030" and the height of the head portion 16 to be about 0.010" to about 0.020". In general, however, the width of the neck portion 14 is less than the width of the head portion 16.

As shown in FIG. 2, after the parison 10 is extruded, the parison 10 is blow molded into the shape of a balloon 18. The balloon 18 may be blow molded inside an open cavity in the mold 20 by applying pressure inside the lumen of the parison 10 and heating the parison 10 and/or mold 20. It may also be desirable to stretch the parison 10 during the blow molding process. As shown, the mold 20 and the blow molded balloon 18 have a working diameter region 22, tapered regions 24 that extend from each end of the working diameter region 22, and neck regions 26 that extend from the end of each of the tapered regions 24. If desired, cavities may be provided in the mold 20 to accommodate the dilation beads 12 from the extruded parison 10. The cavities may be sized to provide sufficient clearance for the dilation beads 12 during the blow molding process so that the size and shape of the dilation beads 12 do not change during the blow molding. Alternatively, cavities may be provided for the dilation beads 12 with a size that reforms the dilation beads 12 from the size and shape of the extruded dilation beads 12.

As shown in FIGS. 3A-3B, part of the dilation beads 12 are removed by a laser 28 after the balloon 18 is blow molded. The blow molded balloon 18 is mounted on a mandrel 30 by extending the mandrel 30 through the inner lumen of the neck regions 26 of the balloon 18. Preferably, the mandrel 30 is connected to a computer controlled rotational motor 32 for rotating the mandrel 30 and blow molded balloon 18 in a controlled manner. The mandrel 30 and rotational motor 32 are preferably mounted on a computer controlled linear travel bed 34 for translating the mandrel 30 and blow molded balloon 18 in a controlled manner. The laser 28 is preferably mounted above the mandrel 30 and linear bed 34 so that the laser beam 36 is directed downwards towards the blow molded balloon 18. However, it is also possible to arrange the laser 28, rotational motor 32 and linear bed 34 in other arrangements that provide the ability to rotate and translate the blow molded balloon 18 relative to the laser beam 36. In general, however, the blow molded balloon 18 is oriented 90° from the laser beam 36, with the laser beam 36 being offset from the axis of the blow molded balloon 18.

Preferably, the laser beam 36 is positioned so that the width of the laser beam 36 covers the entire height of the head portion 16 but only part of the neck portion of the dilation beads 12. Thus, when the laser beam 36 is activated, the laser 28 fully ablates the entire head portion 16 of the beads 12 and ablates part of the neck portion 14 of the beads 12. As a result, part 38 of the neck portion 14 of the beads 12 remains on the blow molded balloon 18 after laser 28 removal of the dilation bead 12. Although it is possible that the edge of the laser beam 36 may ablate the entire neck portion 14 or almost all of the neck portion 14 along particular regions, it is preferred that the height of the remaining neck portion 38 be about half the height of the original neck portion 14. This height for the remaining neck portion 38 provides a sufficient safety margin to prevent ablating into the neck region 26 and/or tapered regions 24 of the blow molded balloon 18. The remaining height 38 of the neck portion 14 also provides an acceptable amount of remaining material for reforming into the neck regions 26 as described below.

Various types of lasers 28 are known in the art, such as YAG and $CO_2$ lasers. Any of the well-known lasers 28 in the art may be suitable to remove the dilation beads 12 from the balloon 18 by ablation. However, in order to ablate the entire head portion 16 and part of the neck portion 14 of the dilation bead 12, it may be desirable for the width of the laser beam 36 to be about 0.020" to about 0.045". In addition, it may be desirable for the laser beam 36 to have a wavelength of about 10 μm to about 12 μm; a focal length of about 3 mm to about 10 mm; and the power to be about 1 W to about 2 W. The rate of travel of the laser beam 36 may be about 0.1 mm/s to about 1 mm/s in order to concentrate sufficient energy on the head portion 16 and neck portion 14 to achieve acceptable ablation. As understood by those of skill in the art, the rate of travel may be achieved by moving the laser 28 and/or the linear bed 34.

During the laser 28 removal process, the laser beam 36 and mandrel 30 are translated relative to each other while the laser 28 is activated as described above. Preferably, the dilation beads 12 are completely removed from both of the neck regions 26 of the balloon 18, except for the remaining height part 38 of the neck portions 14. In addition, it may be desirable to remove the dilation beads 12 from at least part of the tapered regions 24 of the balloon 18. However, because the tapered regions 24 are oriented at an angle from the mandrel 30 and the neck regions 26, the offset between the laser beam 36 and the mandrel 30 must be changed in addition to translating the laser 28. It is particularly desirable to remove the dilation beads 12 from the transition regions between the neck regions 26 and the tapered regions 24 since this is an area where the additional material of the dilation beads 12 tends to bunch up and interfere with folding of the balloon 18 in use. However, if the dilation beads 12 are removed from the tapered regions 24, it is desirable to leave part 38 of the neck portion 14 on the balloon 18 as described above to avoid ablating into the body portion of the balloon 18.

One method for removing the dilation beads 12 involves removing an entire section of one dilation bead 12 and then rotating the mandrel 32 to another dilation bead 12. In this method, it is important to initially align the blow molded balloon 18 on the mandrel 30 and/or the mandrel 30 with the rotational motor 32 to ensure that the first dilation bead is oriented at 90° from the laser beam 36. The dilation bead 12 may then be ablated by translating the laser beam 36 relative to the mandrel 30 without rotating the laser 28 or mandrel 30. After the entire length of the dilation bead 12 to be removed has been ablated, the rotational motor 32 may index the mandrel 30 and balloon 18 so that a different dilation bead 12 is oriented at 90° from the laser beam 36. This process of translating and rotating can be repeated as needed to remove all of the desired sections of the dilation beads 12.

Alternatively, multiple dilation beads 12 may be removed at the same time by simultaneously rotating and translating the laser beam 36 relative to the mandrel 30 and balloon 18. In this approach, the laser beam 36 may follow a generally helical path along the length of the neck regions 26 and/or tapered regions 24. In other words, the mandrel 30 may rotate so that the entire circumference of the balloon 18 is exposed to the laser beam 36 during one full rotation of the mandrel 30. As a result, the laser beam 36 ablates a small section of each dilation bead 12 during each rotation. During subsequent rotations, adjacent small sections are ablated and so on until the entire length of the dilation beads 12 to be removed have been ablated. In addition to a helical path of travel, the mandrel 30 may be rotated one revolution without translating the laser 28. The laser 28 may then be translated a small step before the next revolution and so on. Preferably, the laser 28 is translated a distance that is less than the width of the laser beam 36 during each rotation. As a result, the path of the laser beam 36 will overlap slightly with each revolution to ensure that the entire length of the dilation beads 12 is removed. If it is the desirable to speed up the laser 28 removal process, it may be possible to speed up rotation of the mandrel 30 between the dilation beads 12 where the laser 28 is not ablating any material. However, if this is desirable, it will be necessary to rotationally align the dilation beads 12 and the laser 28 when the balloon 18 is mounted on the mandrel 30. However, if the rotational speed remains constant, an advantage of rotating and translating together, either in a helical relationship or a step pattern, is that no alignment of the dilation beads 12 and laser 28 are needed. This may make the setup process easier and improve the quality of the removal process.

After the dilation beads 12 have been removed, the balloon 18 is removed from the mandrel 30. A catheter 40 may then be inserted through the neck regions 26 of the blow molded balloon 18. The catheter 40 is then affixed to the inner lumen of the neck regions 26 to seal the neck regions 26 to the catheter 40. One process that may be used to affix the neck regions 26 to the catheter 40 is melt bonding. In this process, heat shrink tubing 42 is disposed over the neck regions 26. The heat shrink tubing 42, neck regions 26 and catheter 40 are then heated. The heat softens the neck regions 26 and the catheter 40 and causes the heat shrink tubing 42 to shrink and squeeze the neck regions 26 and the catheter 40 together. As a result, the neck regions 26 and the catheter 40 melt together and adhere to each other when the heat shrink tubing 42, neck regions 26 and catheter 40 cool. In addition, the part 38 of the neck portions 14 that remained on the balloon 18 after the dilation beads 12 were removed are reformed into the body of the balloon 18 by the pressure of the heat shrink tubing 42 and the softening caused by the heat. Preferably, the heat shrink tubing 42 is removed from the neck regions 26 after the melt bonding. This provides a smooth attachment between the catheter 40 and the balloon 18 without any significant remnant of the dilation beads 12 in the neck regions 26 and/or tapered regions 24.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A method of manufacturing a balloon catheter, comprising:
    extruding a parison comprising a bead along an entire length of an outer surface of said parison, said bead comprising a head portion and a neck portion connecting said head region to said outer surface;
    blow molding said parison to form an expanded balloon configuration comprising a working diameter region, a tapered region at each end of said working diameter region, and a neck region at each end of said tapered regions, said working diameter region being larger in diameter than said neck regions and said tapered regions providing transitions between said working diameter region and said neck regions; wherein said neck portion of said bead comprises a width less than a width of said head portion of said bead after blow molding;
    mounting the blow molded balloon on a mandrel extending through an inner lumen of said neck regions;
    positioning said mandrel and said blow molded balloon relative to a laser beam so that said laser beam is oriented 90° from said mandrel and is offset from said mandrel so that a width of said laser beam covers the entirety of said head portion and only part of said neck portion;
    translating said laser beam and said mandrel relative to each other while said laser beam is activated, said laser beam thereby passing along each of said neck regions and ablating the entirety of said head portion and only part of said neck portion along said neck regions, a part of said neck portion remaining on said neck regions after ablating said bead;
    removing said mandrel from said blow molded balloon after ablating said bead; and
    inserting a catheter through said inner lumen of said neck regions and bonding said neck regions to said catheter.

2. The method according to claim 1, further comprising rotating said laser beam and said mandrel relative to each other at the same time said laser beam and said mandrel are translated relative to each other, wherein more than one of said bead disposed around a circumference of said neck regions are partially ablated during each full rotation.

3. The method according to claim 1, further comprising rotating said laser beam and said mandrel a full rotation relative to each other and translating said laser beam and said mandrel relative to each other a distance less than said width of said laser beam for said full rotation, wherein more than one of said bead disposed around a circumference of said neck regions are partially ablated during said full rotation.

4. The method according to claim 1, further comprising translating said laser beam and said mandrel relative to each other, at the same time said offset between said laser beam and said mandrel is changed, said laser beam thereby passing along at least part of said tapered regions and ablating the entirety of said head portion and only part of said neck portion along said tapered regions, a part of said neck portion remaining on said tapered regions after ablating said bead.

5. The method according to claim 1, further comprising disposing heat shrink tubing over said neck regions after said catheter is inserted through said inner lumen of said neck regions and heating said heat shrink tubing and said neck regions, said part of said neck portion remaining on said neck regions after ablating said beam thereby being substantially reformed into said neck regions.

6. The method according to claim 1, wherein said parison is extruded from a nylon material.

7. The method according to claim 1, wherein said width of said neck portion is about 0.010" to about 0.020" and said width of said head portion is about 0.015" to about 0.030".

8. The method according to claim 1, wherein a height of said neck portion is about 0.010" to about 0.025" and a height of said head portion is about 0.010" to about 0.020".

9. The method according to claim 1, wherein said width of said laser beam is about 0.020" to about 0.045".

10. The method according to claim 1, wherein a wavelength of said laser beam is about 10 μm to about 12 μm.

11. The method according to claim 1, wherein a focal length of said laser beam is about 3 mm to about 10 mm.

12. The method according to claim 1, wherein a power of said laser beam is about 1 W to about 2 W.

13. The method according to claim 1, wherein a rate of travel of said laser beam is about 0.1 mm/s to about 1 mm/s.

14. The method according to claim 1, further comprising rotating said laser beam and said mandrel a full rotation relative to each other and translating said laser beam and said mandrel relative to each other a distance less than said width of said laser beam for said full rotation, wherein more than one of said bead disposed around a circumference of said neck regions are partially ablated during said full rotation, and disposing heat shrink tubing over said neck regions after said catheter is inserted through said inner lumen of said neck regions and heating said heat shrink tubing and said neck regions, said part of said neck portion remaining on said neck regions after ablating said beam thereby being substantially reformed into said neck regions.

15. The method according to claim 14, further comprising translating said laser beam and said mandrel relative to each other, at the same time said offset between said laser beam and said mandrel is changed, said laser beam thereby passing along at least part of said tapered regions and ablating the entirety of said head portion and only part of said neck portion along said tapered regions, a part of said neck portion remaining on said tapered regions after ablating said bead.

16. The method according to claim 15, wherein said parison is extruded from a nylon material, said width of said neck portion being about 0.010" to about 0.020", said width of said head portion being about 0.015" to about 0.030", a height of said neck portion being about 0.010" to about 0.025", a height of said head portion being about 0.010" to about 0.020", and said width of said laser beam being about 0.020" to about 0.045".

17. The method according to claim 16, wherein a wavelength of said laser beam is about 10 μm to about 12 μm, a focal length of said laser beam is about 3 mm to about 10 mm, a power of said laser beam is about 1 W to about 2 W, and a rate of travel of said laser beam is about 0.1 mm/s to about 1 mm/s.

18. The method according to claim 1, wherein said parison is extruded from a nylon material, said width of said neck portion being about 0.010" to about 0.020", said width of said head portion being about 0.015" to about 0.030", a height of said neck portion being about 0.010" to about 0.025", and a height of said head portion being about 0.010" to about 0.020".

19. The method according to claim 18, wherein said width of said laser beam is about 0.020" to about 0.045", a wavelength of said laser beam is about 10 μm to about 12 μm, a focal length of said laser beam is about 3 mm to about 10 mm, and a power of said laser beam is about 1 W to about 2 W.

20. The method according to claim 19, further comprising disposing heat shrink tubing over said neck regions after said catheter is inserted through said inner lumen of said neck regions and heating said heat shrink tubing and said neck regions, said part of said neck portion remaining on said neck regions after ablating said beam thereby being substantially reformed into said neck regions.

\* \* \* \* \*